(12) United States Patent
Yoshinaga

(10) Patent No.: US 9,917,420 B2
(45) Date of Patent: Mar. 13, 2018

(54) QUANTUM CASCADE LASER INTEGRATED DEVICE

(71) Applicant: SUMITOMO ELECTRIC INDUSTRIES, LTD., Osaka (JP)

(72) Inventor: Hiroyuki Yoshinaga, Yokohama (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/608,664

(22) Filed: May 30, 2017

(65) Prior Publication Data

US 2017/0353009 A1   Dec. 7, 2017

(30) Foreign Application Priority Data

Jun. 2, 2016   (JP) ................. 2016-111022

(51) Int. Cl.
| | |
|---|---|
| *H01S 5/34* | (2006.01) |
| *H01S 5/12* | (2006.01) |
| *G01N 21/17* | (2006.01) |
| *H05B 37/02* | (2006.01) |
| *G01N 21/39* | (2006.01) |
| *B82Y 20/00* | (2011.01) |
| *H01S 5/40* | (2006.01) |
| *H01S 5/22* | (2006.01) |
| *H01S 5/20* | (2006.01) |

(52) U.S. Cl.
CPC ............ *H01S 5/3401* (2013.01); *B82Y 20/00* (2013.01); *G01N 21/1702* (2013.01); *G01N 21/39* (2013.01); *H01S 5/12* (2013.01); *H01S 5/20* (2013.01); *H01S 5/22* (2013.01); *H01S 5/4087* (2013.01); *H05B 37/02* (2013.01); *G01N 2021/1704* (2013.01)

(58) Field of Classification Search
CPC . H01S 5/20; H01S 5/22; H01S 5/3401; H01S 5/12; H01S 5/4087; B82Y 20/00; G01N 21/1702; G01N 21/39; G01N 2021/1704; H05B 37/02
See application file for complete search history.

(56) References Cited

FOREIGN PATENT DOCUMENTS

| JP | 2010-514163 | 4/2010 |
|---|---|---|
| WO | 2008/127454 | 10/2008 |

*Primary Examiner* — Armando Rodriguez
(74) *Attorney, Agent, or Firm* — Smith, Gambrell & Russell, LLP.

(57) ABSTRACT

A quantum cascade laser integrated device includes: first and second lower semiconductor mesas extending in a direction of a first axis; a covering region disposed on top and side faces of the first and second lower semiconductor mesas, and including first and second upper semiconductor mesas, the first and second upper semiconductor mesas extending in the direction of the first axis on the first and second lower semiconductor mesas, respectively; and first and second electrodes respectively disposed on the upper semiconductor mesas, the first lower semiconductor mesa and the second lower semiconductor mesa each including a quantum cascading core layer, the covering region including a current blocking semiconductor region embedding the first and second lower semiconductor mesas, and a first conductivity-type semiconductor region disposed on the first and second lower semiconductor mesas and the current blocking semiconductor region, and the first conductivity-type semiconductor region including an upper cladding region.

5 Claims, 13 Drawing Sheets

QUANTUM CASCADE LASER INTEGRATED DEVICE

BACKGROUND OF THE INVENTION

Field of the Invention

The present invention relates to a quantum cascade laser integrated device. This application claims the benefit of priority from Japanese Patent application No. 2016-111022 filed on Jun. 2, 2016, which is herein incorporated by reference in its entirety.

Related Background Art

Japanese Unexamined Patent Application Publication (Translation of PCT Application) No. 2010-514163 discloses a quantum cascade semiconductor laser.

SUMMARY OF THE INVENTION

A quantum cascade laser integrated device according to one aspect of the present invention includes: a first lower semiconductor mesa extending in a direction of a first axis; a second lower semiconductor mesa extending in the direction of the first axis; a covering region disposed on top and side faces of each of the first lower semiconductor mesa and the second lower semiconductor mesa, the covering region including a first upper semiconductor mesa and a second upper semiconductor mesa extending in the direction of the first axis on the first lower semiconductor mesa and the second lower semiconductor mesa, respectively; a first electrode disposed on the first upper semiconductor mesa; and a second electrode disposed on the second upper semiconductor mesa, the first lower semiconductor mesa and the second lower semiconductor mesa each including a core layer for quantum cascading, the covering region including a current blocking semiconductor region and a first conductivity-type semiconductor region, the current blocking semiconductor region embedding the first lower semiconductor mesa and the second lower semiconductor mesa, the first conductivity-type semiconductor region being disposed on the first lower semiconductor mesa, the second lower semiconductor mesa, and the current blocking semiconductor region, the first upper semiconductor mesa and the second upper semiconductor mesa being separated from each other, and the first conductivity-type semiconductor region including an upper cladding region.

BRIEF DESCRIPTION OF THE DRAWINGS

The above-described objects and the other objects, features, and advantages of the present invention become more apparent from the following detailed description of the preferred embodiments of the present invention proceeding with reference to the attached drawings.

DESCRIPTION OF THE EMBODIMENTS

Figure 1:
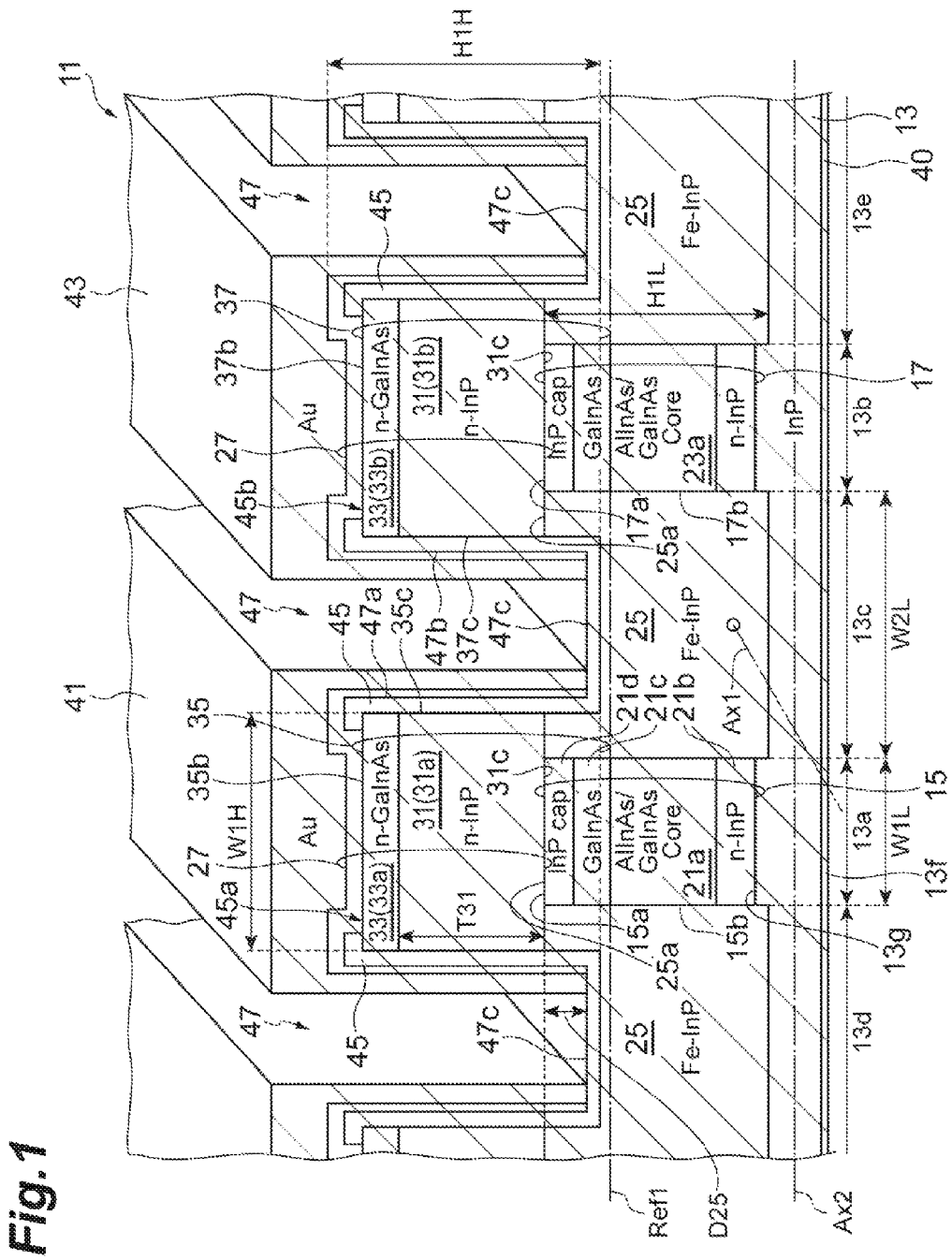
FIG. 1 is a schematic view showing a quantum cascade laser integrated device according to an embodiment of the present invention.

Studies conducted by the inventor reveal that enabling a higher optical output in a quantum cascade semiconductor laser requires the quantum cascade semiconductor laser to have a thick core layer and that confining lasing light into the thick core layer requires the quantum cascade semiconductor laser to have a thick cladding layer. These requirements both cause the quantum cascade semiconductor laser to makes a mesa structure high. According to an estimate carried out by the inventor, the mesa structure including the core layer and the upper cladding layer with respective desired thicknesses has a height of about 10 micrometers. Forming the high mesa structure imposes burdens on etching, and prevents the quantum cascade semiconductor laser thus fabricated from demonstrating an improvement in the performance thereof.

One aspect of the present invention is to provide a quantum cascade semiconductor laser integrated device with a structure allowing the quantum cascade semiconductor laser to have a core layer of a desired thickness and a cladding layer of a desired thickness.

Specific embodiments according to the present aspect will be described below.

A quantum cascade laser integrated device according to an embodiment includes: (a) a first lower semiconductor mesa extending in a direction of a first axis; (b) a second lower semiconductor mesa extending in the direction of the first axis; (c) a covering region disposed on top and side faces of each of the first lower semiconductor mesa and the second lower semiconductor mesa, the covering region including a first upper semiconductor mesa and a second upper semiconductor mesa extending in the direction of the first axis on the first lower semiconductor mesa and the second lower semiconductor mesa, respectively; (d) a first electrode disposed on the first upper semiconductor mesa; and (e) a second electrode disposed on the second upper semiconductor mesa, the first lower semiconductor mesa and the second lower semiconductor mesa each including a core layer for quantum cascading, the covering region including a current blocking semiconductor region and a first conductivity-type semiconductor region, the current blocking semiconductor region embedding the first lower semiconductor mesa and the second lower semiconductor mesa, the first conductivity-type semiconductor region being disposed on the first lower semiconductor mesa, the second lower semiconductor mesa and the current blocking semiconductor region, the first upper semiconductor mesa and the second upper semiconductor mesa being separated from each other, and the first conductivity-type semiconductor region including an upper cladding region.

The quantum cascade laser integrated device allows the current blocking semiconductor region in the covering region to confine current to each of the first and second lower semiconductor mesas. The covering region includes the first and second upper semiconductor mesas extending in the direction of the first axis along the first and second lower semiconductor mesas, respectively. The first and second upper semiconductor mesas are disposed on the first and second lower semiconductor mesas, respectively, to form respective stacking arrangements of the first upper and lower semiconductor mesas and the second upper and lower semiconductor mesas. These stacking arrangements make it possible to provide each of the first and second lower semiconductor mesas with the core layer of a desired thickness and to provide the upper cladding layer with a thickness required for optical confinement.

In the quantum cascade laser integrated device according to an embodiment, the covering region further includes an insulating layer and a groove, the insulating layer covers sides of the first upper semiconductor mesa and the second upper semiconductor mesa, and the groove has a first side, a second side and a bottom, and the first electrode and the second electrode are disposed on the first side and the second side of the groove.

In the quantum cascade laser integrated device, the first and second electrodes that are disposed on the first and second sides of the groove, respectively, can contribute to the transfer of heat from the lower semiconductor mesas.

In the quantum cascade laser integrated device according to an embodiment, the first upper semiconductor mesa and the second upper semiconductor mesa each have a bottom located in the current blocking semiconductor region.

In the quantum cascade laser integrated device, the groove in the current blocking semiconductor region can contribute to the dissipation of heat from the lower semiconductor mesas.

In the quantum cascade laser integrated device according to an embodiment, the first upper semiconductor mesa and the second upper semiconductor mesa has a bottom located inside the upper cladding region.

The quantum cascade laser integrated device provides the covering region with the first conductivity-type semiconductor region that allows light propagating in the semiconductor waveguide to spread thereto.

In the quantum cascade laser integrated device according to an embodiment, the first upper semiconductor mesa and the second upper semiconductor mesa has a bottom located at a top of the upper cladding region.

In the quantum cascade laser integrated device, the covering region allows light propagating in the semiconductor waveguide to spread therein.

Teachings of the present invention can be readily understood by considering the following detailed description with reference to the accompanying drawings shown as examples. Referring to the accompanying drawings, embodiments of a quantum cascade laser integrated device and a method for fabricating a quantum cascade laser integrated device according to the present invention will be described. To facilitate understanding, identical reference numerals are used, where possible, to designate identical elements that are common to the figures.

Figure 2:
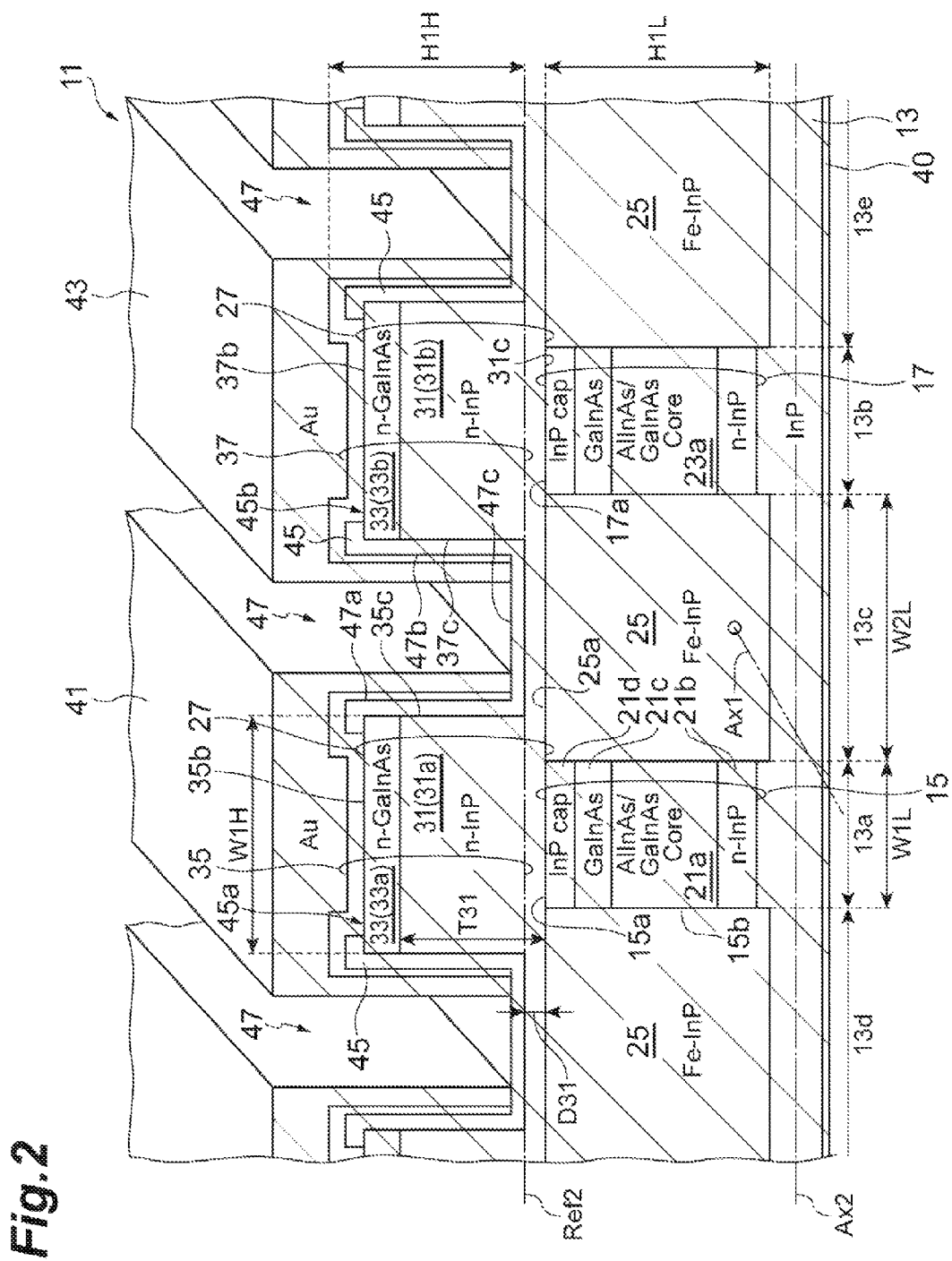
FIG. 2 is a schematic view showing a quantum cascade laser integrated device according to an embodiment of the present invention.
Figure 3:
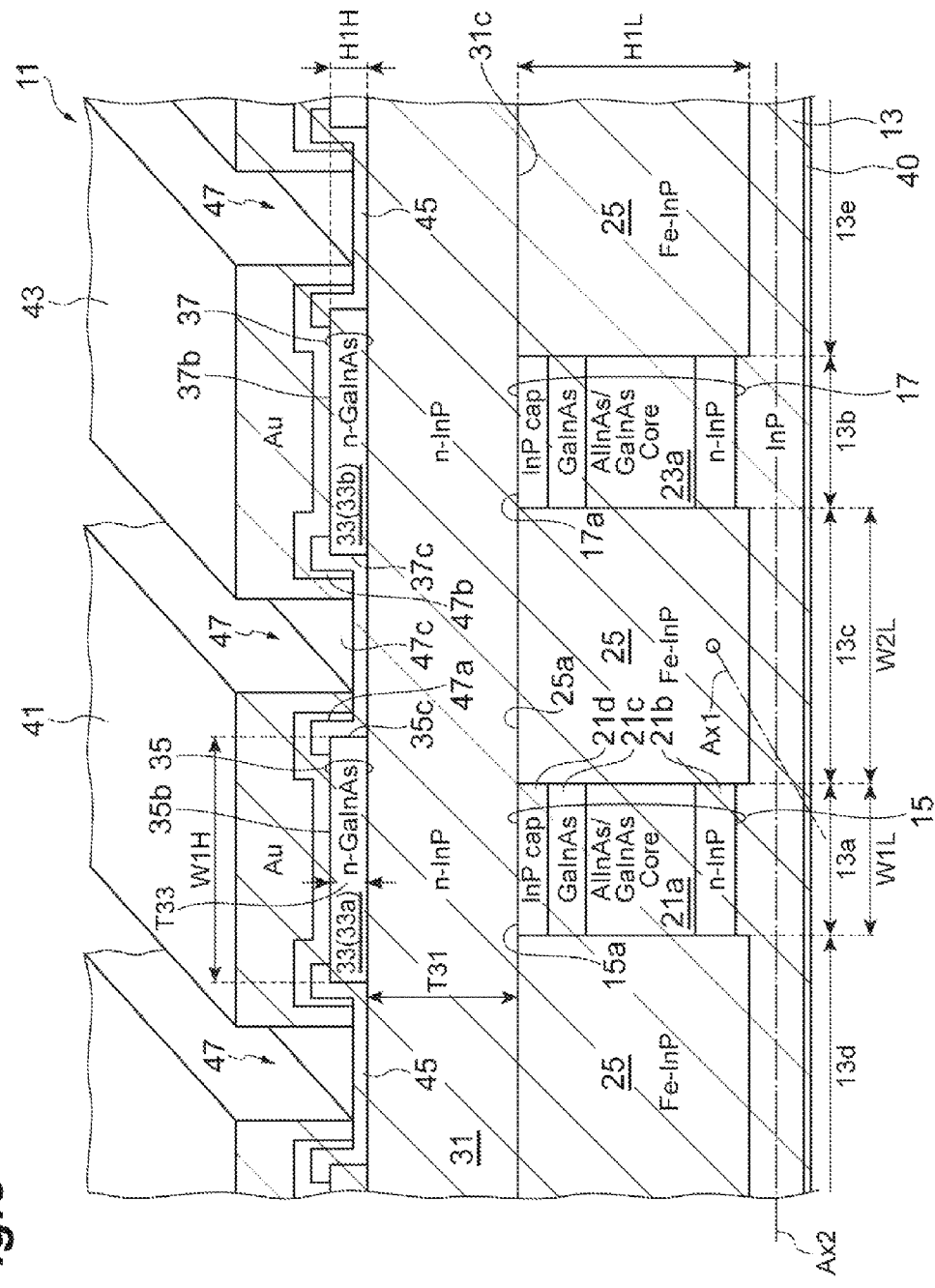
FIG. 3 is a schematic view showing a quantum cascade laser integrated device according to an embodiment of the present invention.

FIGS. 1 to 3 are schematic views each showing a quantum cascade laser integrated device according to the present embodiment. The quantum cascade laser integrated device 11 includes a substrate 13, a first lower semiconductor mesa 15, a second lower semiconductor mesa 17, and a covering region 19. Each of the first lower semiconductor mesa 15 and the second lower semiconductor mesa 17 includes a first core layer 21a and a second core layer 23a, and the first lower semiconductor mesa 15 and the second lower semiconductor mesa 17 extend in the direction of a first axis Ax1. The substrate 13 includes a first region 13a, a second region 13b, a third region 13c, a fourth region 13d, and a fifth region 13e. The third region 13c is disposed between the first region 13a and the second region 13b; the first region 13a is disposed between the third region 13c and the fourth region 13d; and the second region 13b is disposed between the third region 13c and the fifth region 13e. The first region 13a, the second region 13b, the third region 13c, the fourth region 13d, and the fifth region 13e are sequentially arranged in a direction of a second axis Ax2 intersecting the first axis Ax1. In the present embodiment, the first region 13a, the second region 13b, the third region 13c, the fourth region 13d, and the fifth region 13e are arranged such that each of these regions is in direct contact with one or two regions adjacent thereto. The first lower semiconductor mesa 15 and the second lower semiconductor mesa 17 are disposed on the principal surfaces of the first region 13a and the second region 13b, respectively. The covering region 19 is disposed on the principal surfaces of the third region 13c, the fourth region 13d, and the fifth region 13e to cover the top and side faces 15a and 15b of the first lower semiconductor mesa 15 and the top and side faces 17a and 17b of the second lower semiconductor mesa 17. The covering region 19 also includes a current blocking semiconductor region 25 and a first conductivity-type semiconductor region 27. The first conductivity-type semiconductor region 27 includes an upper cladding layer 31, and may further include, for example, a contact layer 33. The covering region 19 has a first upper semiconductor mesa 35 and a second upper semiconductor mesa 37. The covering region 19 covers the top and side faces 15a and 15b of the first lower semiconductor mesa 15, and the top and side faces 17a and 17b of the second lower semiconductor mesa 17. The first conductivity-type semiconductor region 27 is disposed on the first lower semiconductor mesa 15, the second lower semiconductor mesa 17 and the current blocking semiconductor region 25. The first upper semiconductor mesa 35 and the second upper semiconductor mesa 37 extend in the direction of the first axis Ax1 on the first lower semiconductor mesa 15 and the second lower semiconductor mesa 17, respectively. The first lower semiconductor mesa 15 and the second lower semiconductor mesa 17 are separated apart from each other, and the current blocking semiconductor region 25 is disposed between the first lower semiconductor mesa 15 and the second lower semiconductor mesa 17 to ensure electrical insulation therebetween. One of the first upper semiconductor mesa 35 and the second upper semiconductor mesa 37 is spaced from the other.

The quantum cascade laser integrated device 11 allows the covering region 19 to have the current blocking semiconductor region 25 confining current into each of the first lower semiconductor mesa 15 and the second lower semiconductor mesa 17. The first upper semiconductor mesa 35 and the second upper semiconductor mesa 37 in the covering region 19 are disposed on the first lower semiconductor mesa 15 and the second lower semiconductor mesa 17, respectively, to extend in the direction of the first axis Ax1. The first upper semiconductor mesa 35 and the second upper semiconductor mesa 37 are disposed along the first lower semiconductor mesa 15 and the second lower semiconductor mesa 17, respectively, to form both a stacking arrangement of the first upper semiconductor mesa 35 and the first lower semiconductor mesa 15 and a stacking arrangement of the second upper semiconductor mesa 37 and the second lower semiconductor mesa 17. These stacking arrangements allow the first lower semiconductor mesa 15 and the second lower semiconductor mesa 17 to have the first core layer 21a of a desired thickness and the second core layer 23a of a desired thickness, respectively, and can provide the upper cladding layer 31 with a desired thickness enabling optical confinement into the first and second lower semiconductor mesas 15 and 17.

The first upper semiconductor mesa 35 is disposed on the first lower semiconductor mesa 15, and extends along the first lower semiconductor mesa 15. The top 15a of the first lower semiconductor mesa 15 supports the upper cladding layer 31 of the first upper semiconductor mesa 35. In the present embodiment, the top 15a of the first lower semiconductor mesa 15 makes direct contact with the lower face 31c of the upper cladding layer 31. In addition, the second upper semiconductor mesa 37 is disposed on the second lower semiconductor mesa 17, and extends along the second lower semiconductor mesa 17. The top 17a of the second lower semiconductor mesa 17 supports the upper cladding layer 31 of the second upper semiconductor mesa 37. In the present embodiment, the top 17a of the second lower semiconductor mesa 17 makes direct contact with the lower face 31c of the upper cladding layer 31.

The quantum cascade laser integrated device 11 includes a first electrode 41, a second electrode 43, and an insulating layer 45. The first electrode 41 and the second electrode 43 are disposed on the first upper semiconductor mesa 35 and the second upper semiconductor mesa 37, respectively. The insulating layer 45 covers the upper face of the covering region 19 and is provided to enable passivation. The first electrode 41 extends along the first upper semiconductor mesa 35, and makes direct contact with the top 35b of the first upper semiconductor mesa 35 through the first opening 45a of the insulating layer 45. The second electrode 43 extends along the second upper semiconductor mesa 37, and makes direct contact with the top 37b of the second upper semiconductor mesa 37 through the second opening 45b of the insulating layer 45. The first electrode 41 extends on the top and side faces of the insulating layer 45 and is disposed in the first opening 45a. The second electrode 43 extends on the top and side faces of the insulating layer 45 and is disposed in the second opening 45b.

The covering region 19 includes a groove 47 disposed between the first upper semiconductor mesa 35 and the second upper semiconductor mesa 37 and separating them from each other. The insulating layer 45 is disposed in contact with the side 35c of the first upper semiconductor mesa 35 and the side 37c of the second upper semiconductor mesa 37 so as not to fill the groove 47 therewith, and extends on the current blocking semiconductor region 25.

The first upper semiconductor mesa 35 has an upper-mesa width W1H larger than the lower-mesa width W1L of the top face 15a of the first lower semiconductor mesa 15. The lower face 31c of the upper cladding layer 31 in the first upper semiconductor mesa 35 is in direct contact with the top face 15a of the first lower semiconductor mesa 15 in the first region 13a, and is in direct contact with the upper face 25a of the current blocking semiconductor region 25 in the third region 13c and the fourth region 13d.

The second upper semiconductor mesa 37 has a width larger than that of the top face 17a of the second lower semiconductor mesa 17. The lower face 31c of the upper cladding layer 31 in the second upper semiconductor mesa 37 is in direct contact with the top face 17a of the second lower semiconductor mesa 17 in the second area 13b, and is in direct contact with the top face 25a of the current blocking semiconductor region 25 in the third region 13c and the fifth region 13e.

Carriers flowing in an upper semiconductor mesa, such as, the first upper semiconductor mesa 35, pass through the upper cladding layer 31 in the first upper semiconductor mesa 35 having a width larger than that of the top 15a of the first lower semiconductor mesa 15. Providing the first upper semiconductor mesa 35 with the larger width allows the upper cladding layer 31 to have a large thickness. The first upper semiconductor mesa 35 may have such a width as to securely confine light of a long wavelength, which is generated in the core layer in the first lower semiconductor mesa 15, and the width of the first upper semiconductor mesa 35 can be determined independent of the width of the first lower semiconductor mesa 15, and is not restricted by the width and thickness of the first core layer 21a.

The covering region 19 further includes an insulating layer 45, and a groove 47 having a first side face 47a, a second side face 47b and a bottom face 47c, and the insulating layer 45 covers the top faces of the first upper semiconductor mesa 35 and the second upper semiconductor mesa 37. Specifically, the insulating layer 45 covers the side face 35c of the first upper semiconductor mesa 35 and the side face 37c of the second upper semiconductor mesa 37, and is disposed on the current blocking semiconductor region 25. The insulating layer 45 extends so as to define the groove 47. The first electrode 41 and the second electrode 43 extend in the direction of the first axis Ax1, and widen in the direction of the second axis Ax2 to reach the groove 47 and terminate therein.

An exemplary quantum cascade laser integrated device 11.
Substrate 13: n-type InP substrate.
Structures of the first and second lower semiconductor mesas 15 and 17.
First core layer 21a (23a): AlInAs/GaInAs, 2 to 4 micrometer thick.
Lower semiconductor layer 21b (23b): n-type InP, 0.1 to 0.5 micrometer thick.
Upper semiconductor layer 21c (23c): n-type InGaAs diffraction grating layer, 0.3 to 0.6 micrometer thick.
Cap semiconductor layer 21d (23d): n-type InP, 0.01 to 0.1 micrometer thick.
The diffraction grating can be defined as the shape of the interface between the upper semiconductor layer 21c (23c) and the cap semiconductor layer 21d (23d).
Lower-mesa height H1L of each of the first lower semiconductor mesa 15 and the second lower semiconductor mesa 17: 2.5 to 5.5 micrometer high.
Lower-mesa width W1L of each of the first lower semiconductor mesa 15 and the second lower semiconductor mesa 17: 3 to 20 micrometer wide.

The distance W2L between the first lower semiconductor mesa 15 and the second lower semiconductor mesa 17: 30 to 100 micrometer wide.
The first lower semiconductor mesa 15 and the second lower semiconductor mesa 17 each have a bottom located in the substrate 13.
Current blocking semiconductor region 25: Fe-doped InP and/or undoped InP.
Upper-mesa height H1H of each of the first upper semiconductor mesa 35 and the second upper semiconductor mesa 37: 4.1 to 6.3 micrometer wide.
Upper-mesa width W1H of each of the first upper semiconductor mesa 35 and the second upper semiconductor mesa 37: 5 to 30 micrometer wide.
First conductivity-type semiconductor region 27.
Contact layer 33: n-type InGaAs layer, 0.1 to 0.3 micrometer thick.
Insulating layer 45: silicon-based inorganic insulating film, such as, SiON, 0.1 to 0.3 micrometer thick.
In the example, SiON has relatively small light absorption in the wavelength band ranging from 2 to 7 micrometers.
First electrode 41.
Ohmic electrode layer: Ti/Pt/Au.
Metal layer: gold layer (Au plating layer).

The first and second electrodes 41 and 43 are disposed on the first and second side faces 47a and 47b of the groove 47, respectively. The first and second electrodes 41 and 43 are spaced apart from each other on the bottom face 47c. The back face 13f of the substrate 13 is opposite to the principal surface 13g, and mounts a common electrode 40.

Referring to FIG. 1, the first upper semiconductor mesa 35 includes the current blocking semiconductor region 25 on the third region 13c and the fourth region 13d, and an upper portion of the first lower semiconductor mesa 15. The second upper semiconductor mesa 37 includes the current blocking semiconductor region 25 on the third region 13c and the fifth region 13e, and an upper portion of the second lower semiconductor mesa 17. The groove 47 has a bottom located in the current blocking semiconductor region 25. The bottom of the groove 47 is apart from the reference plane Ref1 extending along the upper face of the first core layer 21a of the first lower semiconductor mesa 15 and the second core layer 23a of the second lower semiconductor mesa 17. Light from the first core layer 21a of the first lower semiconductor mesa 15 (the second core layer 23a of the second lower semiconductor mesa 17) propagates in the first lower semiconductor mesa 15 and the current blocking semiconductor region 25. The groove 47 of a large depth contributes to the release of heat generated in the first and second lower semiconductor mesas 15 and 17. The first and second electrodes 41 and 43 have respective ends located on the bottom face 47c of the groove 47. Specifically, the first and second electrodes 41 and 43 are spaced apart from each other on the bottom face 47c. The first and second electrodes 41 and 43 are located on the first and second side faces 47a and 47b of the groove 47, respectively, and can contribute to the dissipation of heat of the lower semiconductor mesas (15, 17).
Thickness T31 of the upper cladding layer 31 (31a, 31b): 3 to 5 micrometers.
Depth D25 of the groove 47 in the current blocking semiconductor region 25: 0.11 to 0.4 micrometers.

As shown in FIG. 2, the bottom of the groove 47 can be in the upper cladding layer 31. The top face of the current blocking semiconductor region 25 is apart from the reference plane Ref2 extending along the bottom of the groove 47. The spread of light propagating in the semiconductor waveguide of the quantum cascade laser integrated device 11 depends on the width of the groove in the covering region 19. The groove 47 can contribute to the release of heat from both the first lower semiconductor mesa 15 and the second lower semiconductor mesa 17. The first electrode 41 and the second electrode 43 have respective side edges located in the groove 47. Specifically, the first electrode 41 and the second electrode 43 are apart from each other on the bottom face 47c of the groove 47. The first electrode 41 and the second electrode 43 are located on the first and second side faces 47a and 47b of the groove 47, respectively, and can contribute to the dissipation of heat from the lower semiconductor mesa (15, 17). The first electrode 41 and the second electrode 43 are terminated in the groove 47, which has a bottom positioned in the upper cladding layer 31, and are separated from the first lower semiconductor mesa 15 and the second lower semiconductor mesa 17. This separation allows the first electrode 41 and the second electrode 43 in the groove 47 to reduce the absorption of the light beams propagating in the first and second lower semiconductor mesas 15 and 17. Further, the first electrode 41 and the second electrode 43 may reach the bottom face 47c of the groove 47, and the first and second electrodes 41 and 43 have respective side edges on the bottom face 47c of the groove 47. The location of the first and second electrodes 41 and 43 enables the dissipation of heat from the lower semiconductor mesa (15, 17).
Thickness T31 of the upper cladding layer 31 (31a, 31b): 3 to 5 micrometers.
The distance D31 between the top of the current blocking semiconductor region 25 and the insulating film on the bottom face 47c of the groove 47: 0.1 to 2 micrometers.

As shown in FIG. 3, the depth of the groove 47 may be equal to the thickness of the contact layer 33 (33a, 33b). The groove 47 is formed to provide the first lower semiconductor mesa 15 and the second lower semiconductor mesa 17 with the respective contact layers isolated from each other, and contributes to the improvement in the device isolation. The upper cladding layer 31 tightly confines light in the semiconductor waveguide of the quantum cascade laser integrated device 11, and separates the first and second lower semiconductor mesas 15 and 17 from the respective contact layers 33 (33a, 33b). The first and second electrodes 41 and 43 have respective ends located in the groove 47. Specifically, the first and second electrode 41 and 43 are spaced apart from each other on the bottom face 47c. The first electrode 41 and the second electrode 43, which are on the first and second sides 47a and 47b of the groove 47, specifically, the sides of the contact layers 33 (33a, 33b), are apart from the respective core layers in the lower semiconductor mesas (15, 17). The first electrode 41 and the second electrode 43 are broadened to the bottom face 47c of the groove 47, and have respective side edges thereon.
Thickness T31 of the upper cladding layer 31 (31a, 31b): 3 to 5 micrometers.
Thickness of the contact layer 33: 0.1 to 0.3 micrometers.

Figure 4:
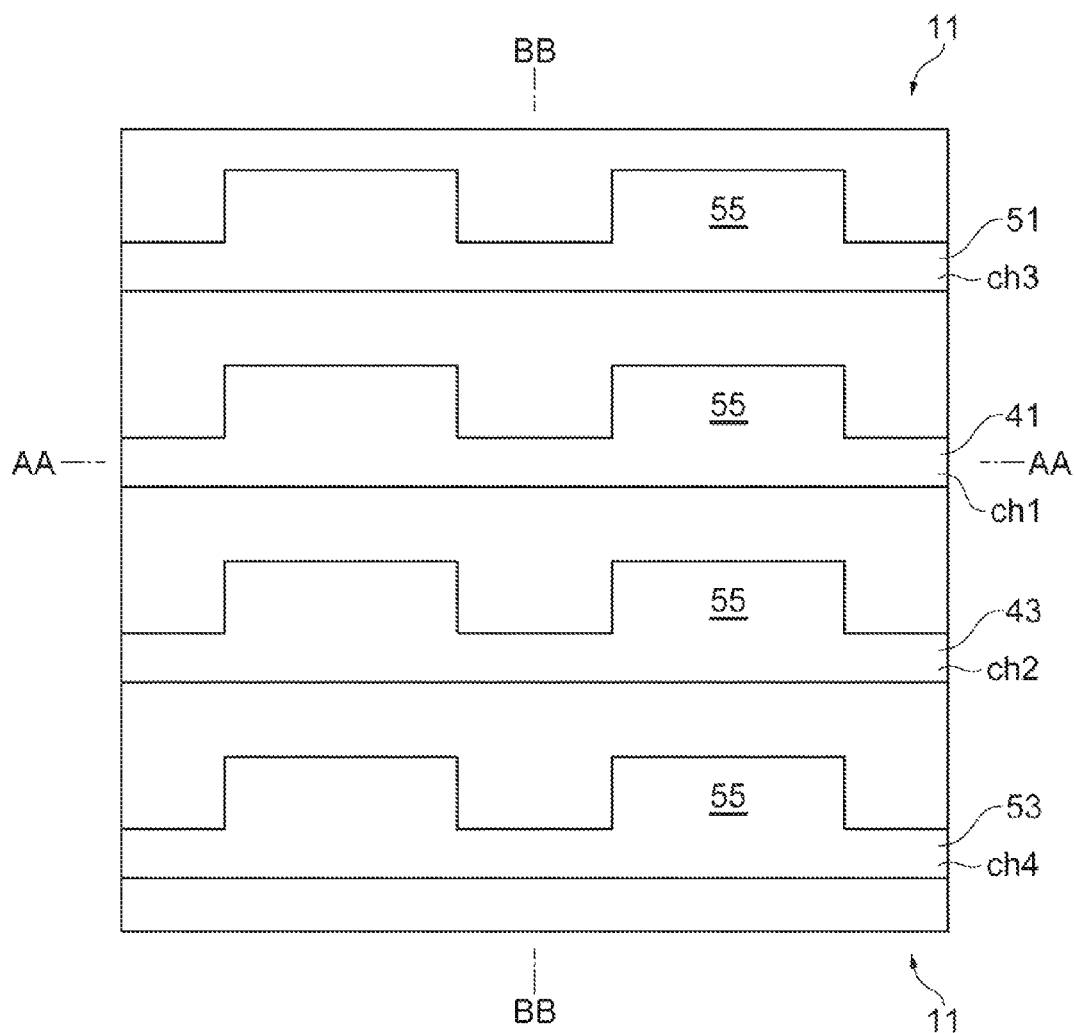
FIG. 4 is a plan view showing the quantum cascade laser integrated devices according to the above embodiments.

FIG. 4 is a plan view showing the top of the quantum cascade laser integrated device. The quantum cascade laser integrated device 11 includes four quantum cascade lasers ch1, ch2, ch3, and ch4. The quantum cascade lasers ch1, ch2, ch3, and ch4 include a first electrode 41, a second electrode 43, a third electrode 51, and a fourth electrode 53, respectively. The quantum cascade lasers ch1 to ch4 include respective upper and lower semiconductor mesas, which are under the first electrode 41, the second electrode 43, the third electrode 51, and the fourth electrode 53. The quantum cascade lasers ch1 to ch4 have respective lower semiconductor mesas, which are buried by the current blocking semiconductor region 25. The quantum cascade lasers ch1 to ch4 also have respective upper semiconductor mesas, which are defined by the grooves 47 disposed in the covering region 19, and specifically, one groove 47 extends to separate the quantum cascade lasers ch1 and ch2 from each other; another groove 47 extends to separate the quantum cascade lasers ch1 and ch3 from each other; and a further groove 47 extends to separate the quantum cascade lasers ch2 and ch4. Yet another groove 47 may be disposed to extend along the outer side of the quantum cascade laser ch3, and still another groove 47 can be disposed to extend along the outer side of the quantum cascade laser ch4. The first electrode 41, the second electrode 43, the third electrode 51, and the fourth electrode 53 are connected to the respective pad electrodes 55. The quantum cascade laser integrated device 11 includes a common electrode 40 disposed on the back face of the substrate 13.

With reference to FIGS. 5 to 13, an exemplary method for fabricating the quantum cascade laser integrated device 11 will be described below. Part (a) in each of FIGS. 5 to 13 is a cross sectional view, taken along a line corresponding to the line AA-AA in FIG. 4, showing a major step in the method, and Part (b) in each of FIGS. 5 to 13 is a cross sectional view, taken along a line corresponding to the line BB-BB in FIG. 4, showing a major step in the method. FIGS. 5-13 each illustrate a single device section of a quantum cascade laser integrated device to be fabricated.

Figure 5:
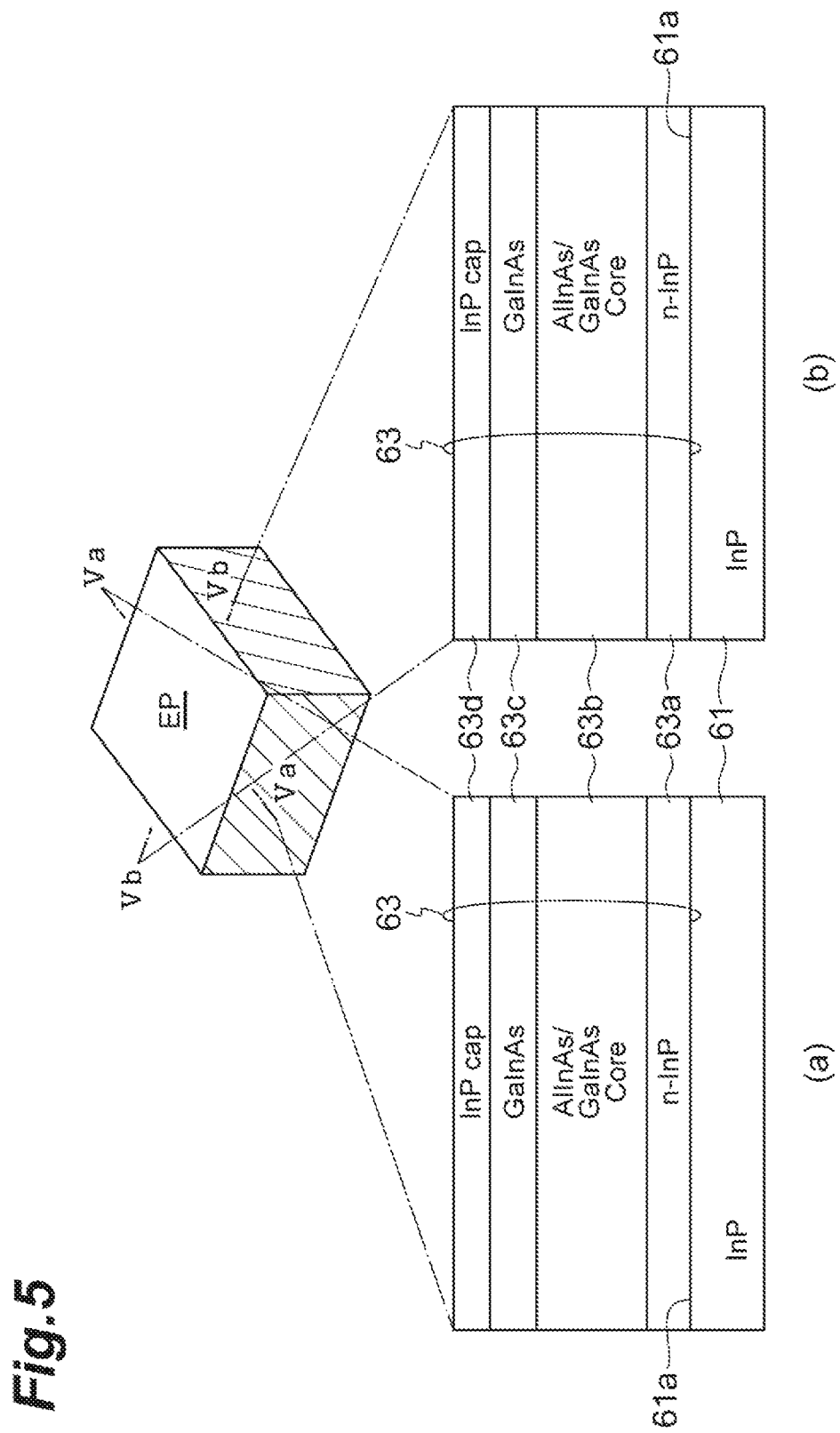
FIG. 5 is a schematic view showing a major step in the method of fabricating the quantum cascade laser integrated device according to the present embodiment.

Part (a) of FIG. 5 shows a cross section taken along the line Va-Va in FIG. 5, and Part (b) of FIG. 5 shows a cross section taken along the line Vb-Vb in FIG. 5. A substrate is prepared for epitaxial growth. In the present embodiment, an n-type InP wafer 61 is used. As shown in FIG. 5, an n-type InP layer 63a, a quantum cascade core layer 63b (AlInAs/GaInAs superlattice), a GaInAs diffraction grating layer 63c, and an InP cap layer 63d are grown to form an epitaxial substrate EP including a laminate 63. This crystal growth can be carried out, for example, by molecular beam epitaxy or organometallic vapor phase epitaxy. The thickness of the laminate 63 can be, for example, 3 to 5 micrometers.

Figure 6:
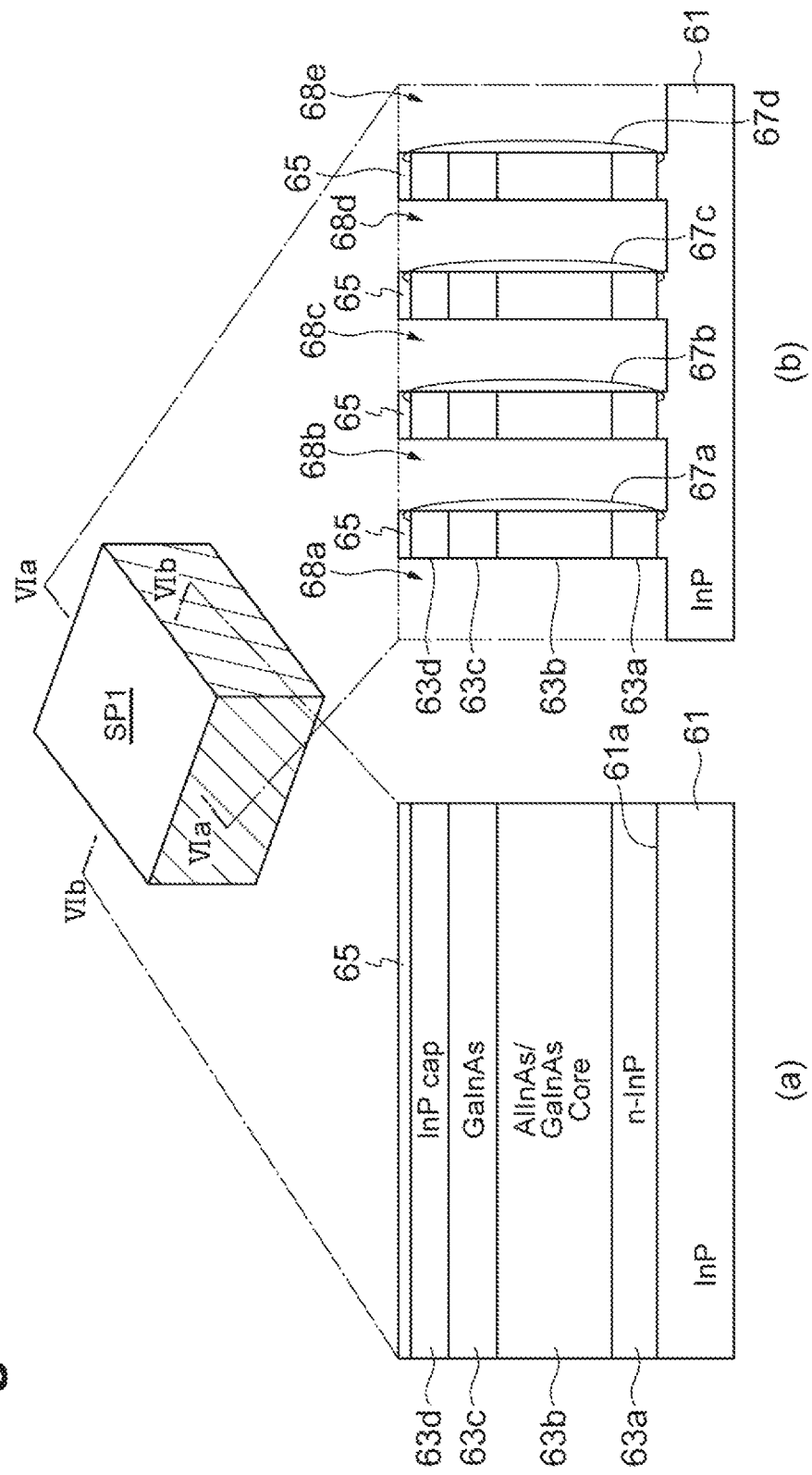
FIG. 6 is a schematic view showing a major step in the method of fabricating the quantum cascade laser integrated device according to the present embodiment.

Part (a) of FIG. 6 shows a cross section taken along the line VIa-VIa in FIG. 6, and Part (b) of FIG. 6 shows a cross section taken along the line VIb-VIb in FIG. 6. As shown in FIG. 6, a first mask 65 (for example, an SiN mask) is formed on the laminate 63, and has a pattern defining the shape of the lower mesas. The laminate 63 is etched with the first mask 65 to form a first substrate product SP1 having lower semiconductor mesas 67a, 67b, 67c and 67d. The first substrate product SP1 has five lower isolation trenches 68a, 68b, 68c, 68d, and 68e that define the lower semiconductor mesas 67a, 67b, 67c, and 67d. The lower isolation trenches 68a, 68b, 68c, 68d, and 68e of the first substrate product SP1 are formed by etching the laminate 63, and have respective bottom faces at which the InP substrate 61 appears. This etching is performed by dry etching using an etchant, such as $SiCl_4$. Specifically, the lower semiconductor mesa 67a is defined by the lower isolation trenches 68a and 68b; the lower semiconductor mesa 67b is defined by the lower isolation trenches 68b and 68c; the lower semiconductor mesa 67c is defined by the lower isolation trenches 68c and 68d; and the lower semiconductor mesa 67d is defined by the lower isolation trenches 68d and 68e. The heights of the lower semiconductor mesas 67a, 67b, 67c, and 67d (the depths of the lower isolation trenches 68a, 68b, 68c, 68d, and 68e) can be in the range of, for example, 3.5 to 5.5 micrometers.

Figure 7:
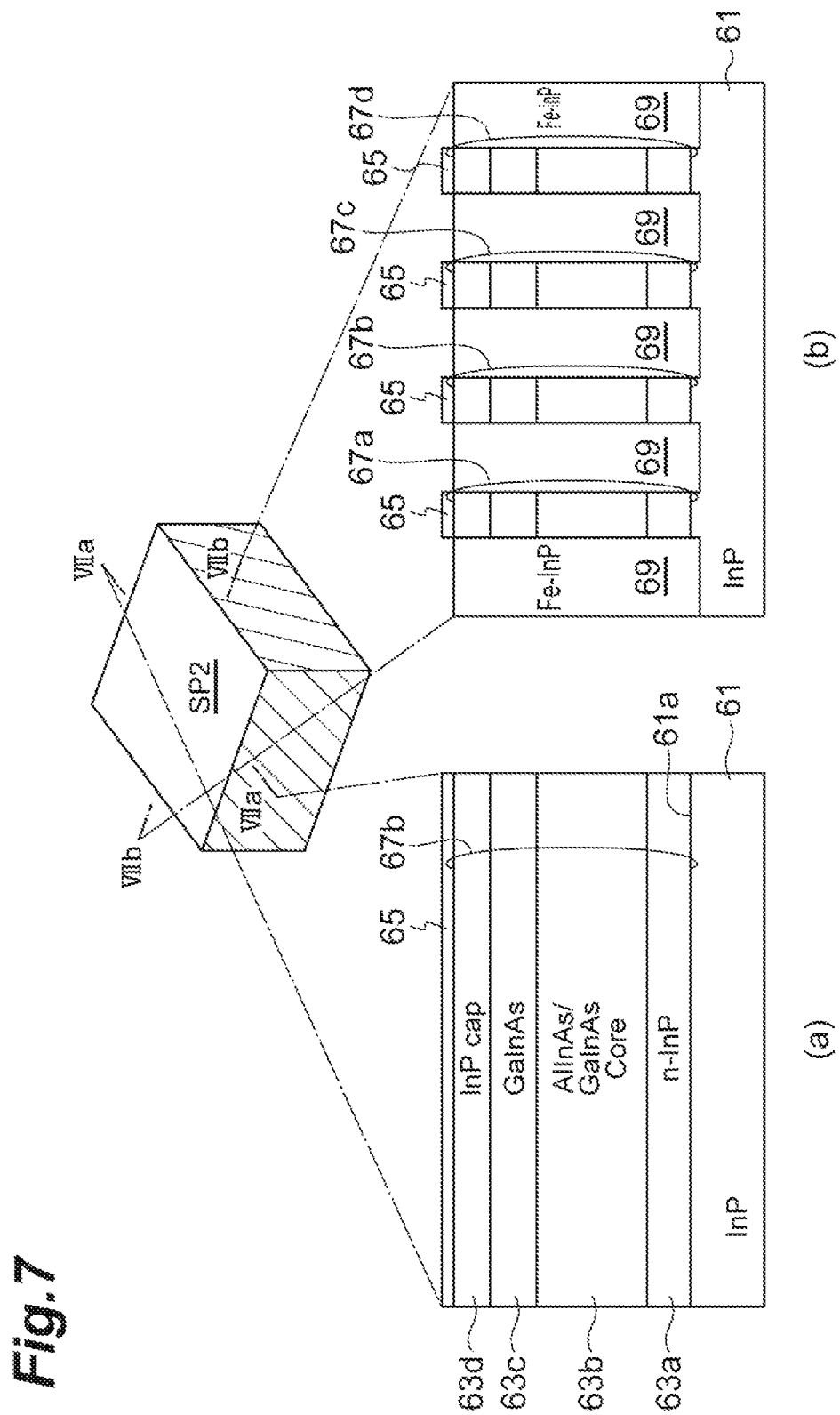
FIG. 7 is a schematic view showing a major step in the method of fabricating the quantum cascade laser integrated device according to the present embodiment.

Part (a) of FIG. 7 shows a cross section taken along the line VIIa-VIIa in FIG. 7, and Part (b) of FIG. 7 shows a cross section taken along the line VIIb-VIIb in FIG. 7. As shown in FIG. 7, the current blocking semiconductor region 69 is grown with the first mask 65, which has not been removed yet, to bury the lower semiconductor mesas 67a, 67b, 67c, and 67d, thereby forming the second substrate product SP2. This crystal growth can be carried out, for example, by molecular beam epitaxy or organometallic vapor phase epitaxy. The current blocking semiconductor region 69 is grown on the side faces of the lower semiconductor mesas 67a, 67b, 67c, and 67d, and the exposed face of the InP substrate 61. The current blocking semiconductor region 69 has such a thickness as to be grown between adjacent two mesas of the lower semiconductor mesas 67a, 67b, 67c, and 67d, so that the lower semiconductor mesas 67a, 67b, 67c, and 67d can be embedded therein. The current blocking semiconductor region 69 may include, for example, Fe-doped InP. The removal of the first mask 65 follows the formation of the current blocking semiconductor region 69.

Figure 8:
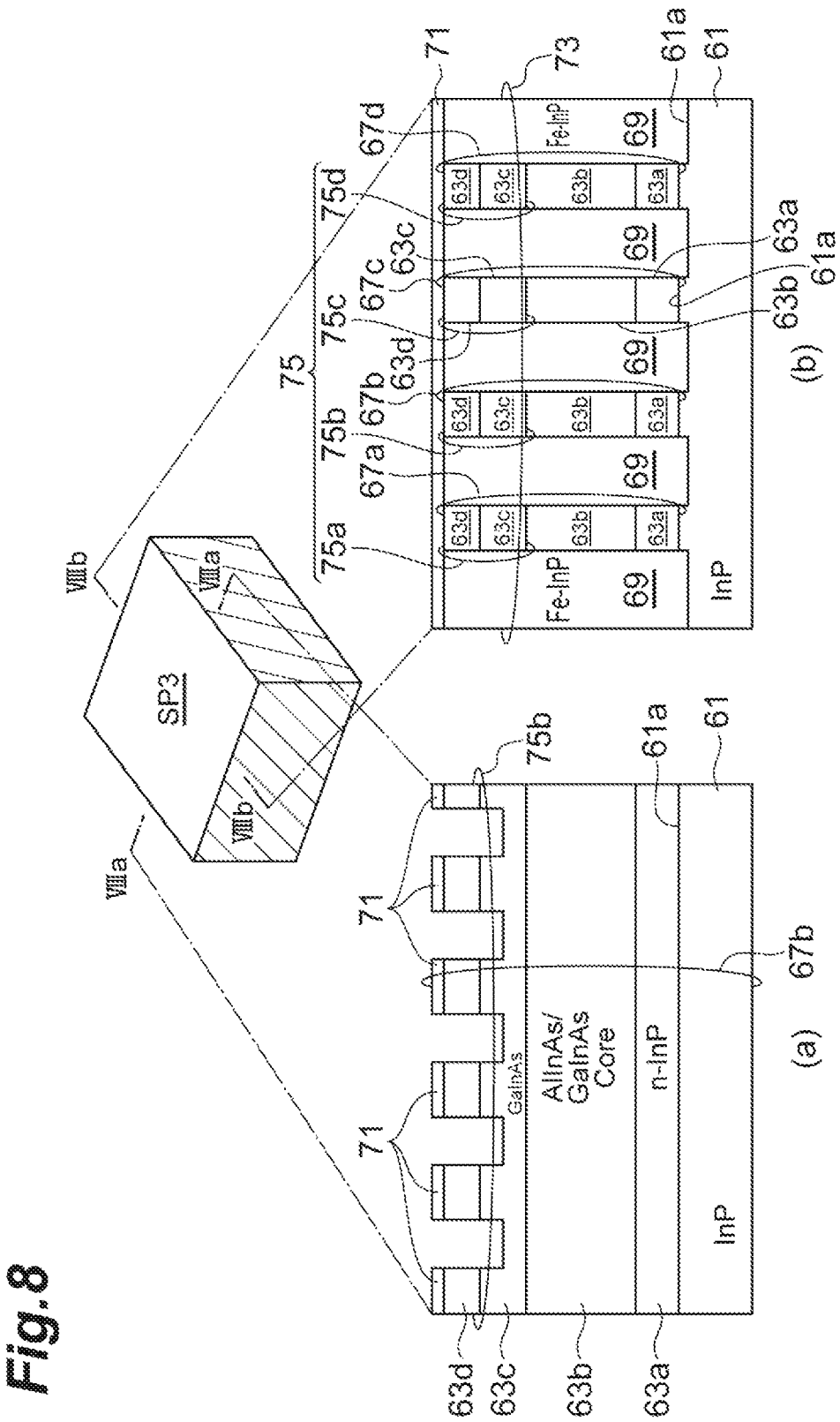
FIG. 8 is a schematic view showing a major step in the method of fabricating the quantum cascade laser integrated device according to the present embodiment.

Part (a) of FIG. 8 shows a cross section taken along the line VIIIa-VIIIa in FIG. 8, and Part (b) of FIG. 8 shows a cross section taken along the line VIIIb-VIIIb in FIG. 8. As shown in FIG. 8, a diffraction grating is formed in the lower semiconductor mesa 67a, 67b, 67c, and 67d. A second mask 71 (for example, an SiN mask) with a pattern defining the diffraction grating is formed on the lower semiconductor mesa 67a, 67b, 67c, and 67d and the current blocking semiconductor region 69 (which are referred to as "underlying semiconductor region 73"), and the underlying semiconductor region 73 is etched with the second mask 71 to form a third substrate product SP3 having the diffraction gratings 75a, 75b, 75c, and 75d in the underlying semiconductor region 73 (specifically, the lower semiconductor mesas 67a, 67b, 67c, and 67d). This etching is performed by dry etching with an etchant, such as $SiCl_4$. The third substrate product SP3 includes a diffraction grating structure 75 having periodic recesses in the GaInAs diffraction grating layer 63c in the underlying semiconductor region 73. Removal of the second mask 71 follows the formation of the patterned diffraction grating structure 75.

Figure 9:
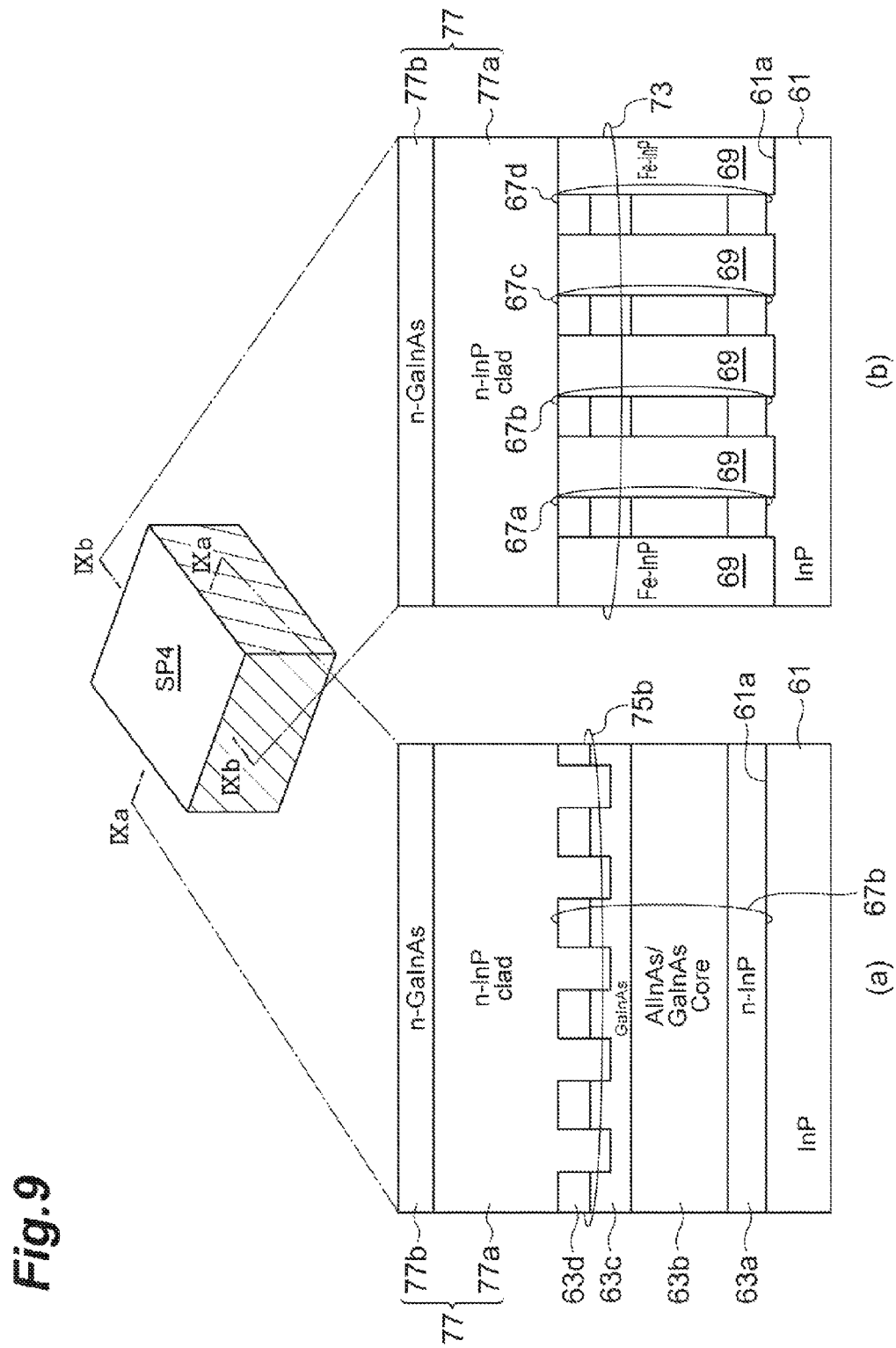
FIG. 9 is a schematic view showing a major step in the method of fabricating the quantum cascade laser integrated device according to the present embodiment.

Part (a) of FIG. 9 shows a cross section taken along the line IXa-IXa in FIG. 9, and Part (b) of FIG. 9 shows a cross section taken along the line IXb-IXb in FIG. 9. As shown in FIG. 9, the first conductivity-type semiconductor region 77 is grown on the patterned diffraction grating structure 75 of the underlying semiconductor region 73 to form the fourth substrate product SP4. This growth can be carried out, for example, by molecular beam epitaxy or organometallic vapor phase epitaxy. In the present embodiment, the first conductivity-type semiconductor region 77 includes an n-type InP upper cladding layer 77a and an n-type InGaAs contact layer 77b. The thickness of the n-type InP upper cladding layer 77a may be, for example, 3 to 5 micrometers, and the thickness of the n-type InGaAs contact layer 77b may be, for example, 0.1 to 0.3 micrometers. The first conductivity-type semiconductor region 77 and the current blocking semiconductor region 69 serve as the covering region 19 of the quantum cascade laser integrated device 11 to be fabricated.

Figure 10:
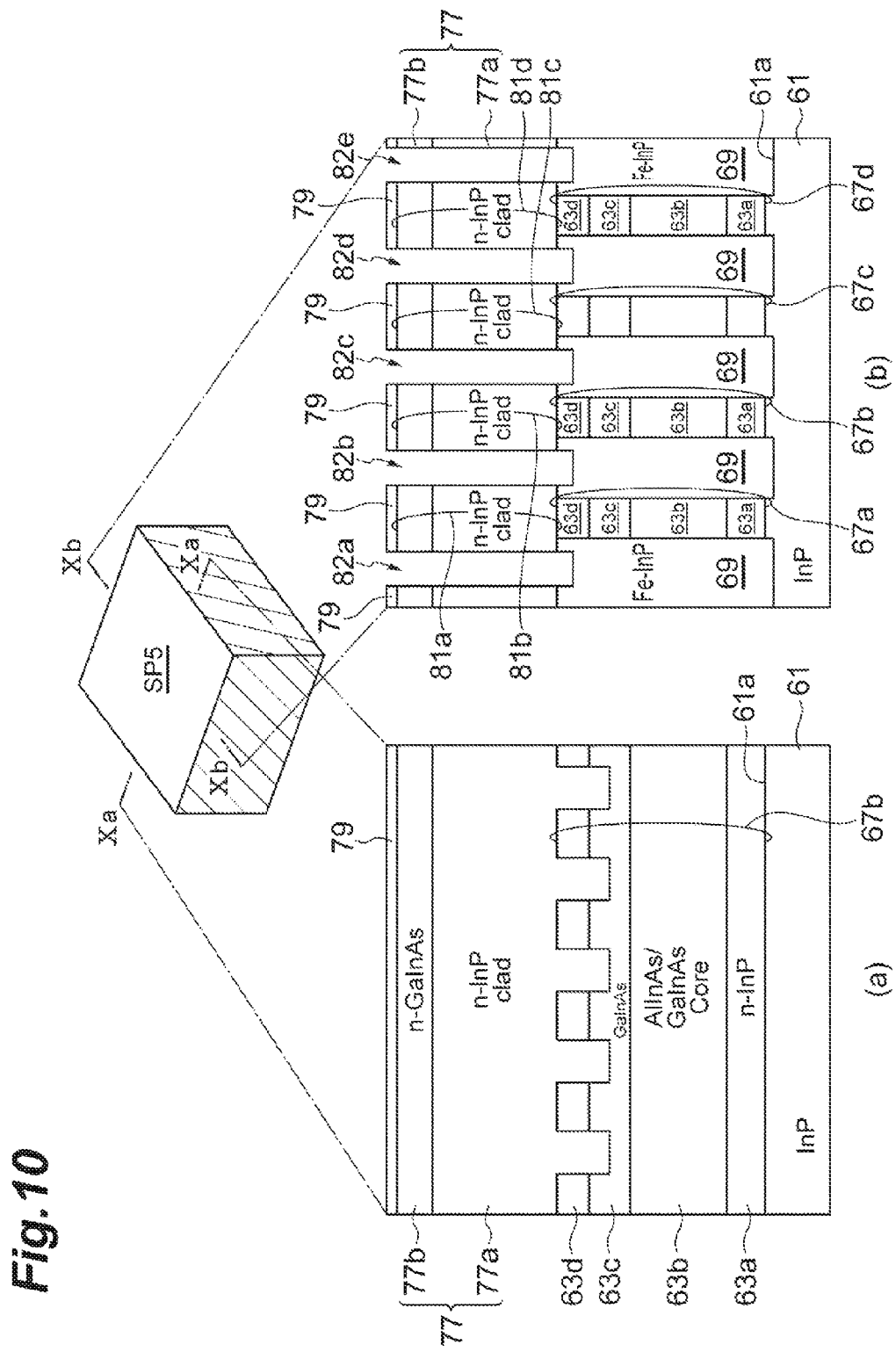
FIG. 10 is a schematic view showing a major step in the method of fabricating the quantum cascade laser integrated device according to the present embodiment.

Part (a) of FIG. 10 shows a cross section taken along the line Xa-Xa in FIG. 10, and Part (b) of FIG. 10 shows a cross section taken along the line Xb-Xb in FIG. 10. As shown in FIG. 10, a third mask 79 (for example, an SiN mask) with a pattern defining the shape of upper isolation trenches is formed on the first conductivity-type semiconductor region 77, and the conductive semiconductor region 77 and/or the current blocking semiconductor region 69 are etched to form a fifth substrate product SP5 having upper semiconductor mesas 81a, 81b, 81c, and 81d. The fifth substrate product SP5 includes isolation trenches 82a, 82b, 82c, 82d, and 82e that define the upper semiconductor mesas 81a, 81b, 81c, and 81d. Specifically, the upper semiconductor mesa 81a is defined by the upper isolation trenches 82a and 82b. The upper semiconductor mesa 81b is defined by the upper isolation trenches 82b and 82c. The upper semiconductor mesa 81c is defined by the upper isolation trenches 82c and 82d. The upper semiconductor mesa 81d is defined by the upper isolation trenches 82d and 82e. The heights of the upper semiconductor mesas 81a, 81b, 81c, and 81d (the depths of the upper isolation trenches 82a, 82b, 82c, 82d, and 82e) can be, for example, in the range of 3.3 to 5.5 micrometers. The upper semiconductor mesas 81a, 81b, 81c, and 81d each have a height, which is associated with the depths of corresponding ones of the upper isolation trenches 82a, 82b, 82c, 82d, and 82e.

Figure 11:
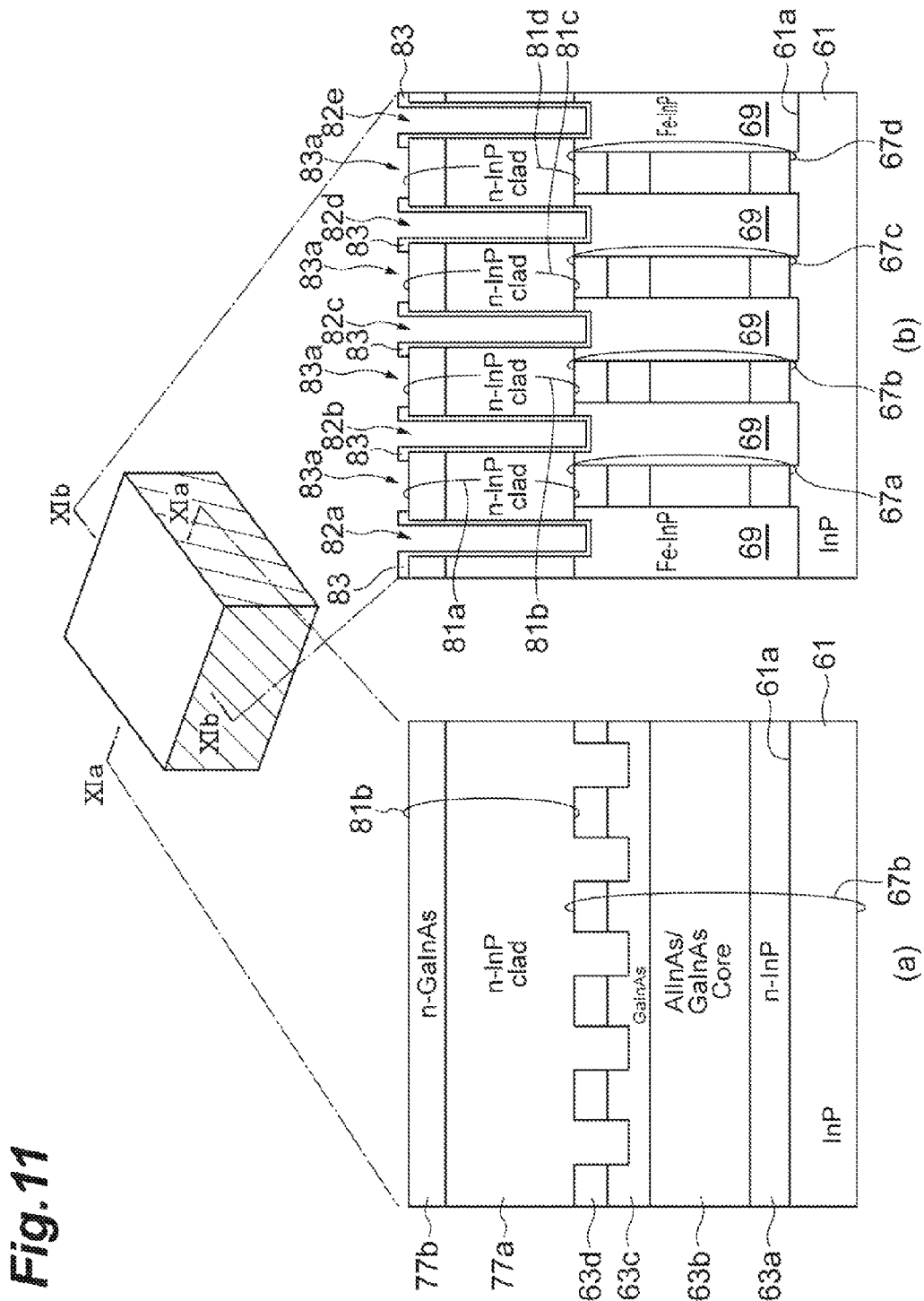
FIG. 11 is a schematic view showing a major step in the method of fabricating the quantum cascade laser integrated device according to the present embodiment.

Part (a) of FIG. 11 shows a cross section taken along the line XIa-XIa in FIG. 11, and Part (b) of FIG. 11 shows a cross section taken along the line XIb-XIb in FIG. 11. As shown in FIG. 11, a passivation film 83 is formed on the fifth substrate product SP5. The passivation film 83 has an opening 83a located on each of the tops of the upper semiconductor mesa 81a, 81b, 81c, and 81d, and covers the top and side faces of the upper semiconductor mesa 81a, 81b, 81c, and 81d, and the side and bottom faces of the trenches 82a, 82b, 82c, 82d, and 82e. The top surface of the passivation film 83, which is on the side faces of two adjacent upper semiconductor mesas of the upper semiconductor mesas 81a, 81b, 81c, and 81d and the bottom face of an upper isolation trench between the two adjacent upper semiconductor mesas, define the groove 47 in the quantum cascade laser integrated device 11 to be fabricated.

Figure 12:
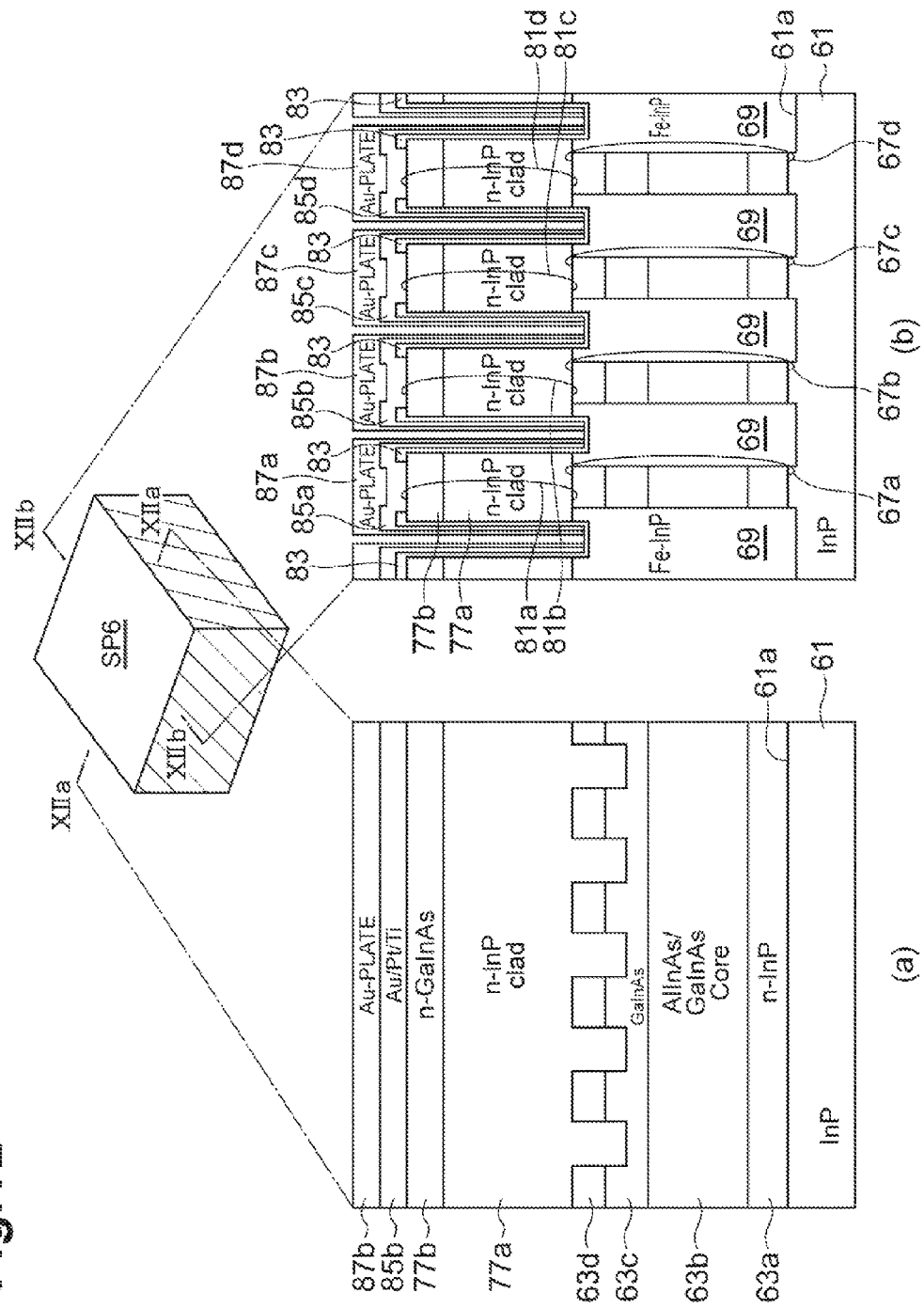
FIG. 12 is a schematic view showing a major step in the method of fabricating the quantum cascade laser integrated device according to the present embodiment.

Part (a) of FIG. 12 shows a cross section taken along the line XIIa-XIIa in FIG. 12, and Part (b) of FIG. 12 shows a cross section taken along the line XIIb-XIIb in FIG. 12. As shown in FIG. 12, ohmic electrodes 85a, 85b, 85c, and 85d for the first electrodes are formed on the top and side faces of the upper semiconductor mesas 81a, 81b, 81c, and 81d, respectively. Each of the ohmic electrodes 85a, 85b, 85c, and 85d includes, for example, an Au/Pt/Ti structure. The Au/Pt/Ti structure is deposited by, for example, sputtering. Next, plating electrodes 87a, 87b, 87c, and 87d for the first electrodes are formed on the ohmic electrodes 85a, 85b, 85c, and 85d, respectively, to produce the sixth substrate product SP6. Each of the plating electrodes 87a, 87b, 87c, and 87d includes an Au layer, which is formed by, for example, a plating method. The ohmic electrodes 85a, 85b, 85c, and 85d and the plating electrodes 87a, 87b, 87c, and 87d are disposed on the top and side faces of the upper semiconductor mesas 81a, 81b, 81c, and 81d, respectively, so as not to bury the upper isolation trenches.

Figure 13:
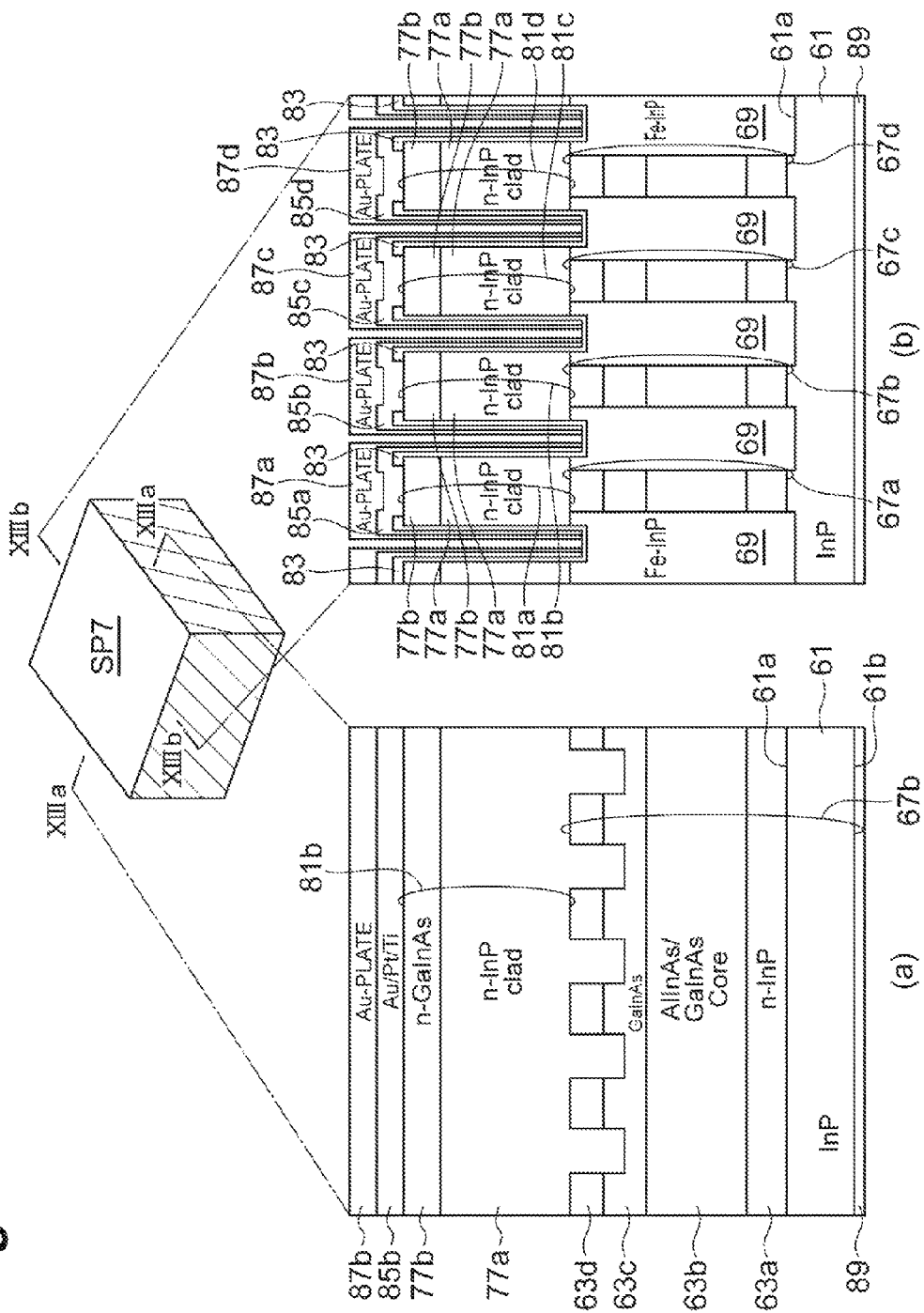
FIG. 13 is a schematic view showing a major step in the method of fabricating the quantum cascade laser integrated device according to the present embodiment.

Part (a) of FIG. 13 shows a cross section taken along the line XIIIa-XIIIa in FIG. 13, and Part (b) of FIG. 13 shows a cross section taken along the line XIIIb-XIIIb in FIG. 13. As shown in FIG. 13, the sixth substrate product SP6 is processed to form a backside electrode 89 on the back face 61b of the substrate 61 thereof to produce a seventh substrate product SP7. The backside electrode 89 may be made of, for example, an Au/Pt/Ti structure. If necessary, the substrate 61 may be polished to form the back face 61b before forming the backside electrode.

The above fabricating method allows anisotropic etching processes to form mesa structures, each of which includes semiconductor regions (for example, the laminate 63, the first conductivity-type semiconductor region 77 and the current blocking semiconductor region 69) arranged in the direction normal to the substrate to form a stacking arrangement. The stacking arrangement allows each of the mesa structures to have a height required for current confinement and optical confinement. An etching amount in each of the anisotropic dry etching processes is smaller than an etching amount required for forming a structure with a desired height by a single etching.

Having described and illustrated the principle of the invention in a preferred embodiment thereof, it is appreciated by those having skill in the art that the invention can be modified in arrangement and detail without departing from such principles. We therefore claim all modifications and variations coining within the spirit and scope of the following claims.

What is claimed is:

1. A quantum cascade laser integrated device including:
a first lower semiconductor mesa extending in a direction of a first axis;
a second lower semiconductor mesa extending in the direction of the first axis;
a covering region disposed on top and side faces of each of the first lower semiconductor mesa and the second lower semiconductor mesa, the covering region including a first upper semiconductor mesa and a second upper semiconductor mesa extending in the direction of the first axis on the first lower semiconductor mesa and the second lower semiconductor mesa, respectively;
a first electrode disposed on the first upper semiconductor mesa; and
a second electrode disposed on the second upper semiconductor mesa,
the first lower semiconductor mesa and the second lower semiconductor mesa each including a core layer for quantum cascading,
the covering region including a current blocking semiconductor region and a first conductivity-type semiconductor region, the current blocking semiconductor region embedding the first lower semiconductor mesa and the second lower semiconductor mesa, the first conductivity-type semiconductor region being disposed on the first lower semiconductor mesa, the second lower semiconductor mesa and the current blocking semiconductor region,
the first upper semiconductor mesa and the second upper semiconductor mesa being separated from each other, and
the first conductivity-type semiconductor region including an upper cladding region.

2. The quantum cascade laser integrated device according to claim 1,
wherein the covering region further includes an insulating layer and a groove, the insulating layer covers sides of the first upper semiconductor mesa and the second upper semiconductor mesa, and the groove has a first side, a second side and a bottom, and
the first electrode and the second electrode are disposed on the first side and the second side of the groove, repectively.

3. The quantum cascade laser integrated device according to claim 1,
wherein the first upper semiconductor mesa and the second upper semiconductor mesa each have a bottom located in the current blocking semiconductor region.

4. The quantum cascade laser integrated device according to claim 1, wherein the first upper semiconductor mesa and the second upper semiconductor mesa each have a bottom located in the upper cladding region.

5. The quantum cascade laser integrated device according to claim 1,
wherein the first upper semiconductor mesa and the second upper semiconductor mesa each have a bottom located at a top of the upper cladding region.

* * * * *